United States Patent [19]

Minami et al.

[11] Patent Number: 5,342,982
[45] Date of Patent: Aug. 30, 1994

[54] SILICON-CONTAINING ORGANIC COMPOUNDS AND PROCESS FOR PREPARING SAME

[75] Inventors: Masaki Minami, Yokohama; Keizo Ikai, Kanagawa; Mitsuo Matsuno, Yokohama, all of Japan

[73] Assignee: Nippon Oil Company, Limited, Tokyo, Japan

[21] Appl. No.: 82,033

[22] Filed: Jun. 24, 1993

[30] Foreign Application Priority Data

Jun. 25, 1992 [JP] Japan .................................. 4-206923

[51] Int. Cl.⁵ .............................................. C07F 7/08
[52] U.S. Cl. .................................. 556/431; 556/432; 549/4; 549/214; 548/406
[58] Field of Search .................... 556/431, 432; 549/4, 549/214; 548/406

[56] References Cited

U.S. PATENT DOCUMENTS

| | | | |
|---|---|---|---|
| 3,167,528 | 1/1965 | Marsden | 556/431 |
| 3,278,461 | 10/1966 | Wu | 556/432 |
| 3,758,541 | 9/1973 | Chandra et al. | 556/431 |
| 5,001,247 | 3/1991 | Bortolin et al. | 556/431 |
| 5,011,961 | 4/1991 | Bortolin et al. | 556/431 |
| 5,068,381 | 11/1991 | Ito et al. | 556/431 |
| 5,113,002 | 5/1992 | Hamada et al. | 556/431 |
| 5,244,733 | 9/1993 | Kozakai et al. | 556/432 |

*Primary Examiner*—Paul F. Shaver
*Attorney, Agent, or Firm*—St.Onge Steward Johnston & Reens

[57] ABSTRACT

Silicon-containing organic compounds useful as starting materials of functional polymer materials, as well as a process for preparing the same, are provided. The silicon-containing organic compounds are represented by the following general formula:

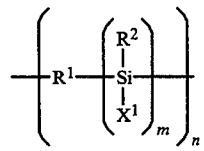

where $R^1$ is a $\pi$ conjugated type divalent organic group having 2 to 30 carbon atoms, $R^2$ is a hydrocarbon group having 1 to 30 carbon atoms, $X^1$ is a halogen atom, m and n satisfy the conditions of $1 \leq m \leq 2$ and $n \geq 2$, respectively. A compound of the above general formula is prepared by reacting an organometallic compound of the following general formula:

$$M^1\text{-}R^1\text{-}M^2$$

where $M^1$ and $M^2$ are each a metal selected from Group 1, 2 and 12 metals in the Periodic Table, with a silane compound of the following general formula:

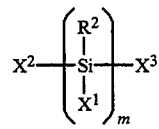

where $R^2$ is a hydrocarbon group having 1 to 30 carbon atoms, $X^1$, $X^2$ and $X^3$ are each a halogen atom.

6 Claims, No Drawings

SILICON-CONTAINING ORGANIC COMPOUNDS AND PROCESS FOR PREPARING SAME

BACKGROUND OF THE INVENTION

The present invention relates to useful and novel silicon-containing organic compounds for use as starting materials of such functional polymer materials as electrically conductive materials and photoresists, and a process for preparing the same.

Recently, polysilanes have been found to have such properties as electrical conductivity and photolyric property, and attempts to use them as electroconductive materials and resist materials have been conducted. Particularly, silicon-containing organic polymers having on the main chains thereof a $\pi$-electron type aromatic ring and silicon have been found to exhibit an electrical conductivity of the semiconductor level upon doping, and attempts to use them as electroconductive materials have been made.

For example, in Japanese Patent Laid Open No.60-8839A there are disclosed a process for preparing poly(-disilanylenephenylene) derivatives and utilization thereof, in which the said polymers are used as resist materials, utilizing the photolyric property thereof, and there is obtained a pattern with a stroke width of 0.5 $\mu$m.

In Japanese Patent Laid Open Nos.3-6231A and 3-6232A it is disclosed that compounds having a high electrical conductivity are obtained by adding a dopant to poly(disilanylenenaphthylene) derivatives. As the said dopant, a Lewis acid such as $SbF_5$ is used thereon. And it is disclosed therein that the said polysilane compounds exhibit an electrical conductivity of $10^{-2}$ to 10 S/cm.

Further, in Japanese Patent Laid Open No.3-146522A it is disclosed that $SbF_5$ is added as a dopant to poly[2,5-(disilanylene)thienylene] derivatives and that the said polysilanes exhibit an electrical conductivity of $10^{-2}$ to 10 S/cm.

In the case of such polysilanes, however, there remain problems to be solved; for example, their photostability is low because they have a photolytic property, the production monomers is not easy, and substituent groups on silicon are limited.

It is an object of the present invention to provide starting compounds (polymers) capable of compensating for the drawbacks, e.g. photolysis, of the above materials and to be used for the production of novel silicon-containing organic polymers which permit introduction of electron withdrawing groups of electron donating groups.

It is another object of the present invention to provide a process for preparing such silicon-containing organic polymers easily and efficiently.

SUMMARY OF THE INVENTION

Having made intensive studies for solving the above-mentioned problems of the prior art, the present inventors found out novel silicon-containing organic compounds and also found out that the said novel compounds could be obtained by the condensation of divalent organometallic compounds and silane compounds. And on the basis of this finding the present invention has been accomplished.

More specifically, the present invention, in one aspect thereof, is concerned with a silicon-containing organic compound represented by the following general formula [1]:

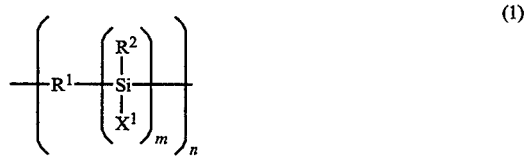

wherein $R^1$ represents a $\pi$ conjugated type divalent organic group having 2 to 30 carbon atoms, $R^2$ represents a hydrocarbon group having 1 to 30 carbon atoms, $X^1$ represents a halogen atom, m is a number in the range of $1 \leq m \leq 2$, and n is a number in the range of $n \geq 2$.

Further, the present invention, in another aspect thereof, is concerned with a process for preparing a silicon-containing organic compound represented by the following general formula [1]:

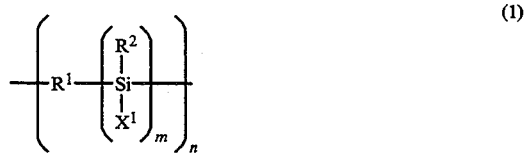

which process is characterized by reacting an organometallic compound of the following general formula [2]:

$$M^1\text{-}R^1\text{-}M^2 \qquad [2]$$

where $R^1$ represents a $\pi$ conjugated type divalent organic group having 2 to 30 carbon atoms, and $M^1$ and $M^2$, which may be the same or different, are each independently a metal group selected from Group 1, 2 and 12 metals in the Periodic Table, with a silane compound of the following general formula [3]:

where $R^2$ is a hydrocarbon group having 1 to 30 carbon atoms, $X^1$, $X^2$ and $X^3$ are each a halogen atom, and m is a number in the range of $1 \leq m \leq 2$.

DETAILED DESCRIPTION OF THE INVENTION

The present invention will be described in detail below.

In the silicon-containing organic compound represented by the general formula [1], $R^1$ is a $\pi$ conjugated type divalent organic group having 2 to 3 carbon atoms.

The $\pi$ conjugated type group as referred to herein indicates a group having a system in which $\pi$ electrons of several carbon-carbon double bonds or triple bonds interact and electrons are localized. In the compound of the present invention, moreover, silicon atom is directly attached to a $\pi$ conjugated system.

As examples of the conjugated type divalent organic group represented by $R^1$ there are mentioned hydrocarbon residues having 2 to 30 carbon atoms such as allylene, heteroallylene, vinylene, butadienylene, ethynylene and butadiynylene.

As allylene groups, those having 6 to 16 carbon atoms are particularly preferred, examples of which include p-phenylene, m-phenylene, 2,4-naphthylene, 2,5-naphthylene, 2,6-naphthylene, 4,4'-biphenylene, 9,10-anthrylene and 2,7-pyrenylene.

As heteroallylene groups, those wherein the hetero atoms is oxygen, sulfur or nitrogen, particularly oxygen or sulfur, and those having 4 to 10 carbon atoms, are preferred. Examples are 2,5-thienylene, 2,5-furanylene, 2,5-pyrolylene and 1,3-benzo[c]thienylene.

Such allylene and heteroallylene groups may have a substituent group which is inert to the organometallic compound of the general formula [2] or the silane compound of the general formula [3]. Such substituent group is not specially limited, but as examples there are mentioned hydrocarbon residues having 1 to 12 carbon atoms. More concrete examples include alkyl groups such as methyl, ethyl and isopropyl, as well as alkoxy groups such as methoxy and ethoxy groups.

The foregoing vinylene and butadienylene groups may have a substituent group inert to the silane compound of the general formula [3]. Such substituent group is not specially limited, but as examples there are mentioned hydrocarbon residues having 1 to 6 carbon atoms. More concrete examples include such alkyl groups as methyl, ethyl, isopropyl and butyl. As examples of vinylene and butadienylene groups having such substituents there are mentioned dimethylvinylene, diethylvinylene, dibutylvinylene, 2,3-dimethylbutadienylene, tetramethylbutadienylene and tetraethylbutadienylene.

As groups containing carbon-carbon triple bond there are mentioned ethynylene and butadiynylene groups.

Further, such allylene, heteroallylene, vinylene, butadienylene, ethynylene and butadiynylene groups may be suitably combined. The following are mentioned as examples:

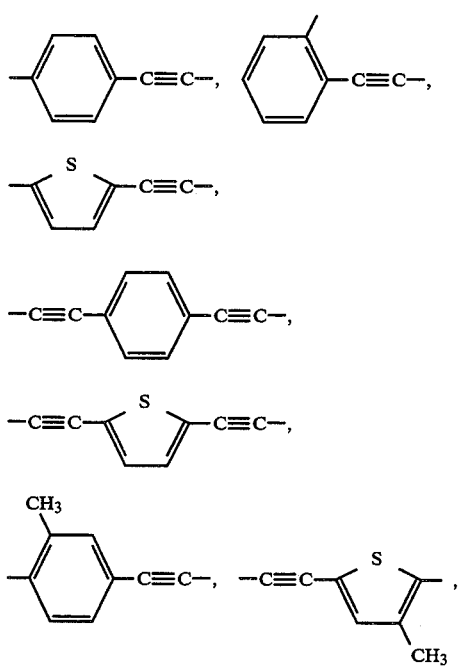

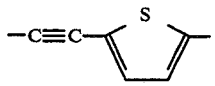

In the silicon-containing organic compound of the general formula [1], $R^2$ represents a hydrocarbon group having 1 to 30, preferably 1 to 22, carbon atoms. As examples of such hydrocarbon group there are mentioned alkyl, aryl and aralkyl groups, preferably alkyl groups having 1 to 12, particularly 1 to 6, carbon atoms, as well as aryl and aralkyl groups having 6 to 30, particularly 6 to 22, carbon atoms. It is optional whether such alkyl groups may be straight-chained or branched. As suitable examples of straight-chained alkyl groups there are mentioned memthyl, ethyl, n-propyl and n-butyl, while as suitable examples of branched alkyl groups there are mentioned isopropyl, sec-butyl, tert-butyl, isopentyl and neopentyl.

Examples of the aforesaid aryl groups include phenyl, naphthyl and anthryl. The aromatic rings contained in these groups may have substituent groups inert to the organometallic compound of the general formula [2] or to the silane compound of the general formula [3]. As examples of such substituent groups there are mentioned hydrocarbon residues having 1 to 12, preferably 1 to 6, carbon atoms. More concrete examples include alkyl groups such as methyl, ethyl and isopropyl, as well as alkoxy groups such as methoxy and ethoxy. As more concrete examples of the aryl groups in question there are mentioned tolyl, xylyl, mesitylyl, cumenyl, methoxyphenyl and ethoxyphenyl.

As examples of the aralkyl groups represented by $R^2$ there are mentioned monovalent aralkyl groups obtained by substituting aliphatic hydrocarbons with at least one aryl group. More concrete examples include benzyl, phenethyl, diphenylmethyl and trityl. The aromatic rings contained in these groups may have substituent groups inert to the silane compound of the general formula [3]. Examples of such substituent groups include hydrocarbon residues having 1 to 12, preferably 1 to 6, carbon atoms, and more concrete examples are alkyl groups such as methyl, ethyl and isopropyl, as well as alkoxy groups such as methoxy and ethoxy. As further examples of the aralkyl groups in question there are mentioned tolylmethyl, xylylmethyl, cumenylmethyl, tritolylmethyl, tri(dimethylphenyl)methyl, methoxyphenylmethyl and diethoxyphenylmethyl.

In the silicon-containing compound of the general formula [1], $X^1$ represents a halogen atom, preferably chlorine, bromine or iodine, m is in the range of $1 \leq m \leq 2$ and n is not smaller than 2, preferably 2 to 10,000, more preferably 5 to 5,000.

The silicon-containing compound of the general formula [1] has an average molecular weight of $2 \times 10^2$ to $1 \times 10^6$, preferably $5 \times 10^2$ to $5 \times 10^6$.

The silicon-containing compound of the general formula [1] is prepared by the reaction, preferably condensation reaction, of an organometallic compound of the following general formula [2]:

$$M^1\text{-}R^1\text{-}M^2 \qquad [2]$$

where $R^1$ is a π conjugated type divalent organic group having 2 to 30 carbon atoms, and $M^1$ and $M^2$, which may be the same or different, are each independently a metal group selected from Group 1, 2 and 12 metals in the Periodic Table, with a silane compound of the following general formula [3]:

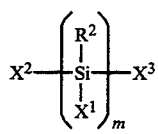

where $R^2$ is a hydrocarbon group having 1 to 30 carbon atoms, $X^2$, $X^2$ and $X^3$ are each a halogen atom, and m is $1 \leq m \leq 2$.

In the organometsllic compound of the general formula [2], as examples of the conjugated type divalent organic group represented by $R^1$ there are mentioned hydrocarbon residues having 2 to 30 carbon atoms such as allylene, heteroallylene, vinylene, butadienylene, ethynylene and butadiynylene.

As such sllylene groups, those having particularly 6 to 16 carbon atoms are preferred. Examples are p-phenylene, m-phenylene, 2,4-naphthylene, 2,5-naphthylene, 2,6-naphthylene, 4,4'-biphenylene, 9,10-anthrylene and 2,7-pyrenylene.

In such heteroallylene groups, it is preferred that the hetero atom contained therein be oxygen, sulfur or nitrogen, more preferably oxygen or sulfur. Particularly, those having 1 to 10 carbon atoms are preferred. Examples are 2,5-thienylene, 2,5-furanylene, 2,5-pyrolylene and 1,3-benzo[c]thienylene.

Such allylene and heteroallylene groups may contain a substituent group which is inert to the organometallic compound of the general formula [2] or to the silane compound of the general formula [3]. The said substituent group is not specially limited, but as examples there are mentioned hydrocarbon residues having 1 to 12 carbon atoms. More concrete examples include alkyl groups such as methyl, ethyl and isopropyl, as well as alkoxy groups such as methoxy and ethoxy.

The above-mentioned vinylene and butadienylene groups may contain a substituent group inert to the silane compound of the general formula [3]. Such substituent group is not specially limited, but as examples there are mentioned hydrocarbon residues having 1 to 6 carbon atoms. More concrete examples include alkyl groups such as methyl, ethyl, isopropyl and butyl. As examples of vinylene and butadienylene groups having such substituent groups there are mentioned dimethylvinylene, diethylvinylene, dibutylvinylene, 2,3-dimethylbutadienylene, tetramethylbutadienylene and tetraethylbutadienylene.

As groups containing carbon-carbon triple bond there are mentioned ethynylene and butadiynylene groups.

These allylene, heteroallylene, vinylene, butadienylene, ethynylene and butadiynylene groups may be suitably combined. The following are mentioned as examples:

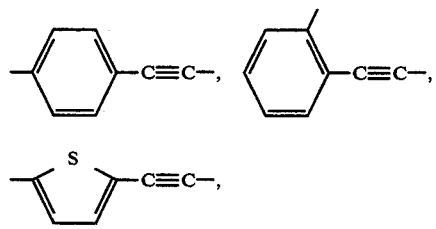

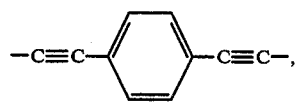

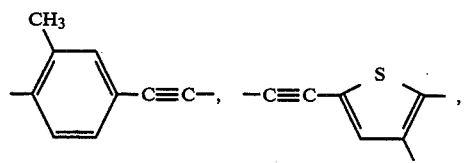

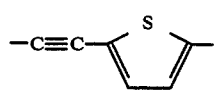

In the organometallic compound of the general formula [2], $M^1$ and $M^2$ are each a metal group selected from Group 1, 2 and 12 metals in the Periodic Table. The "metal group" as referred to herein means a group constituted by metal alone in the case of a monovalent metal, and in the case of a di- or higher valent metal, it means that the metal is attached directly to $R^1$ and that the remaining valence has a suitable group such as halogen or an acid residue. As examples of Group 1 metals there are mentioned such alkali metals as lithium and sodium. As examples of Group 2 metal groups there are mentioned halide groups of such alkaline earth metals as magnesium and calcium. More concrete examples include -MgCl, -MgBr, -MgI, -CaCl, -CaBr and -CaI. As examples of Group 12 metal groups there are mentioned halide groups of such metals as zinc, cadmium and mercury. More concrete examples are -ZnCl, -ZnBr, -ZnI, -CdCl, -CdBr, -HgCl and -HgBr. $M^1$ and $M^2$ may be the same or different.

How to prepare the organometallic compound of the general formula [2] is not specially limited. For example, in the case of an organometallic compound wherein $M^1$ and $M^2$ are each a Group 1 or 2 metal in the Periodic Table, it can be prepared by treating a corresponding organic group, namely, a hydride or halide having the foregoing $R^1$ group, with the metal(s) of $M^1$ and $M^2$ or with an organometallic compound-of the said metal(s) (the organic group being an alkyl, aryl or aralkyl group having 1 to 12 carbon atoms). In the case of an organometallic compound wherein $M^1$ and $M^1$ are each a Group 12 metal in the Periodic Table, it can be prepared by treating the organometallic compound of Group 1 or 2 metal produced by the method just mentioned above, with a halide of a Group 12 metal to effect metal exchange.

The following (1) to (5) are concrete examples of how to prepare organometallic compounds of Group 1 or 2 metals.

(1) Treating a dihalide having the foregoing $R^1$ group with an organolithium reagent [e.g. an alkyllithium such as n-butyllithium (n-BuLi)] or magnesium to prepare an organometallic compound (dilithio reagent or diGrignard reagent) represented by the general formula [2].

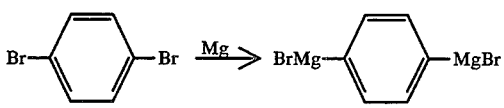

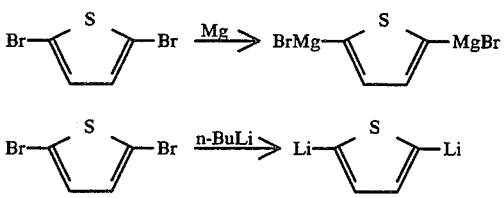

(2) Subjecting acetylene or an acetylene derivative, having R¹, to metal-hydrogen exchange using a Grignard reagent [e.g. ethylmagnesium bromide (EtMgBr)] to prepare an organometallic compound represented by the general formula [2].

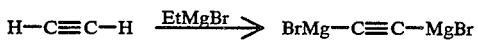

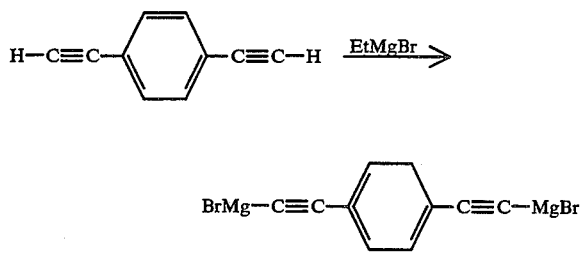

(3) Treating a hydride having R¹ with an organolithium reagent (e.g. alkyllithium such as n-butyllithium) in the presence of an amine [e.g. N,N,N',N'-tetramethylethylenediamine (TMEDA)].

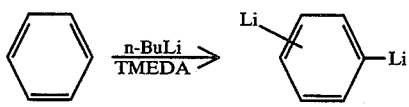

(4) Treating a corresponding hydride having R¹ with a mixture of an organolithium reagent (e.g. alkyllithium such as n-butyllithium) and potassium t-butoxide (t-BuOK).

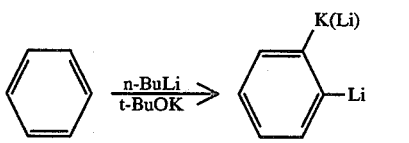

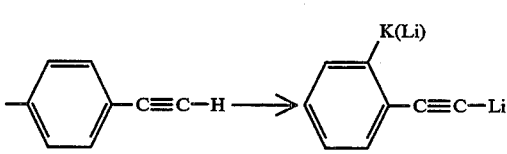

(5) Treating a corresponding hydride or halide having R¹ with an organolithium reagent (e.g. alkyllithium such as n-butyllithium), allowing a hydrogen-metal exchange reaction, including elimination reaction, to take place.

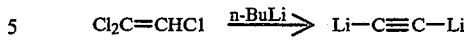

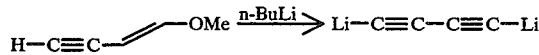

Suitable conditions for the above reactions are selected according to the compounds used, etc. Usually, the reactions are performed at a temperature of −100° C. to 200° C. for 10 minutes to 100 hours in the presence of an aromatic hydrocarbon solvent, a saturated hydrocarbon solvent, an unsaturated hydrocarbon solvent, or an ether solvent.

In the compound represented by the general formula [3], R² is a hydrocarbon group having 1 to 30, preferably 1 to 24, carbon atoms. Examples of such hydrocarbon group include alkyl, aryl and aralkyl groups. Particularly, alkyl groups having 1 to 12, especially 1 to 6, carbon atoms, as well as aryl and aralkyl groups having 6 to 30, especially 6 to 22, carbon atoms, are preferred.

As such alkyl groups, both straight-changed and branched ones are employable. Examples of straight-chained alkyl groups include methyl, ethyl, n-propyl and n-butyl, while examples of branched alkyl groups are isopropyl, sec-butyl, tert-butyl, isopentyl and neopentyl.

As examples of such aryl groups there are mentioned phenyl, naphthyl and anthryl. The aromatic rings contained in these groups may have substituent groups inert to the organometallic compound of the general formula [2]. As examples of such substituent groups there are mentioned alkyl groups such as methyl, ethyl and isopropyl, as well as alkoxy groups such as methoxy and ethoxy. More concrete examples of the aryl groups in question are tolyl, xylyl, mesitylyl, cumenyl, methoxyphenyl and ethoxyphenyl.

As examples of aralkyl groups represented by R² there are mentioned monovalent aralkyl groups obtained by substituting aliphatic hydrocarbons with at least one aryl group. More concrete examples are benzyl, phenethyl, diphenylmethyl and trityl. The aromatic rings contained in these groups may have substituent groups inert to the organometallic compound of the general formula [2]. As examples of such substituent groups there are mentioned hydrocarbon residues having 1 to 12, preferably 1 to 6, carbon atoms, and more concrete examples include alkyl groups such as methyl, ethyl and isopropyl, as well as alkoxy groups such as methoxy and ethoxy. As more concrete examples of the aralkyl groups in question there are mentioned tolylmethyl, xylylmethyl, cumenylmethyl, tritolylmethyl, tri(dimethylphenyl)methyl, methoxyphenylmethyl and diethoxyphenylmethyl.

In the silicon-containing compound of the general formula [3], X¹ represents a halogen atom selected from fluorine, chlorine, bromine and iodine, with chlorine, bromine and iodine being preferred, and m is in the range of $1 \leq m \leq 2$. Even at m=3 or larger, there will occur a similar reaction, but it is difficult to prepare and obtain a silane compound with a value of m exceeding The silane compound of the general formula [3] is usually employed alone (as one kind), but for the purpose of, for example, adjusting the solubility, electrical conductivity and polymerization degree of the silicon-containing organic polymer of the general formula [1], there may be used two or more kinds of such silane compounds having different substituent groups in combination.

The reaction is performed usually by adding a silane compound into an organometallic reagent in the presence of a solvent in an inert atmosphere, followed by stirring.

The silane compound is used usually in an amount such that two chlorine atoms in the silane compound of the general formula [3] react with the divalent organometallic compound of the general formula [2]. Usually, it is desirable that the silane compound be used in an amount of 0.3 to 2.0 moles, preferably 0.7 to 1.2 moles when m=1, or 0.5 to 1.2 moles when m=2, per mole of the organometallic compound.

Examples of employable solvents include aromatic hydrocarbon solvents, saturated hydrocarbon solvents, unsaturated hydrocarbon solvents and ether solvents, which are inert to the organometallic compound and chlorosilane used. Particularly, it is desirable to use aromatic hydrocarbon solvents, e.g. toluene and benzene, and ether solvents, e.g. tetrahydrofuran, which can dissolve the silicon-containing organic compound produced.

As the inert atmosphere there usually is employed an argon atmosphere or a nitrogen atmosphere.

The reaction temperature can be set suitably according to the organometallic compound and silane compound used, but usually it is in the range of $-100°$ to $200°$ C., preferably $-20°$ to $100°$ C.

The reaction time can be set suitably in consideration of the reaction temperature and the amounts of the organometallic reagent and silane compound used, but usually it is in the range of 30 minutes to 200 hours, preferably 1 to 50 hours.

The silicon-containing organic polymer of the general formula [1] thus obtained is usually further treated to effect conversion of the substituent groups on the silicon and is thereby made employable as an electrically conductive material for example. In this case, it is desirable to add a dopant to the silicon-containing organic polymer before use. The dopant is not specially limited. For example, there may be used any of halogens, Lewis acids and transition metal halides which have heretofore been used.

The silicon-containing organic polymer of the general formula [1] can be prepared extremely easily in a single process and that in a high yield (60-100%), using an organic halide or a trichlorosilane which are obtainable easily.

Further, since a highly reactive halogen atom remains on the silicon and easily reacts with organolithium reagent, Grignard reagent and alcohols, it is possible to effect conversion of the substituent groups on the silicon easily.

EXAMPLES

The following examples are given to further illustrate the present invention, but it is to be understood that the invention is not limited at all by those example.

EXAMPLE 1

Preparation of [2,5-(chlorophenylsilanylene)thienylene]

12.7 g (0.060 mole) of phenyltrichlorosilane was added to 2,5-thienylenedimagnesium chloride which had been prepared from 9.2 g (0.060 mole) of 2,5-dichlorothiophene and 2.9 g (0.119 mole) of magnesium in 120 ml of tetrahydrofuran (THF) in a nitrogen atmosphere, followed by heating to reflux for 40 hours.

Thereafter, the solvent was removed, the reaction solution was diluted with dry toluene/n-hexane, and insoluble salt was filtered off, to afford 10.6 g of an oily polymer of yellowish brown. As a result of the following instrumental analysis, this polymer proved to be poly[2,5-(chlorophenylsilanylene)thienylene] (unit 0.028 mole, 78%).

As to the molecular weight of the polymer, GPC measurement was performed after conversion of Si-Cl to Si-Me using methyllithium to find that Mw was 8,600 (degree of polymerization: about 40).

The following are the results of instrumental analysis of the poly[2,5-(chlorophenylsilanylene) thienylene] obtained.

$^1$H-NMR Spectrum (in CDCl$_3$, δ ppm): 7.63–7.78 (m, C$_4$H$_2$S, C$_6$H$_5$).

$^{13}$C-NMR Spectrum (in CDCl, δ ppm): 127.81, 128.16, 132.17, 132.61, 138.69, 139.38.

IR Spectrum (KBr cm$^{-1}$): 3072, 2944, 2876, 1487, 1431, 1270, 1251, 1205, 1015, 812, 741, 700.

Elementary Analysis: Calc'd: C, 53.92; H, 3.17. Found: C, 52.15 H, 3.22.

EXAMPLE 2

Preparation of [2,5-(chloromethylsilanylene)thienylene]

9.0 g (0.060 mole) of methyltrichlorosilane was added to 2,5-thienylenedimagnesium chloride which had been prepared from 9.2 g (0.060 mole) of 2,5-dichlorothiophene and 2.9 g (0.119 mole) of magnesium in 120 ml of tetrahydrofuran (THF) in a nitrogen atmosphere, followed by heating to reflux for 20 hours.

Thereafter, the solvent was removed, the reaction solution was diluted with dry toluene/n-hexane, and insoluble salt was filtered off, to afford 7.3 g of an oily polymer of brown color. As a result of the following instrumental analysis, the polymer proved to be poly[2,5-(chloromethylsilanylene)thienylene] (unit 0.025 mole, 76%).

As to the molecular weight of the polymer, GPC measurement was performed after conversion of Si-Cl to Si-Me using methyllithium to find that Mw was 7,800 (degree of polymerization: about 50).

The following are the results of instrumental analysis of the poly[2,5-(chloromethylsilanylene) thienylene] obtained.

$^1$H-NMR Spectrum (in CDCl$_3$, δ ppm): 0.32 (s, Si-CH$_3$), 7.26 (s, C$_4$H$_2$S).

$^{13}$C-NMR Spectrum (in CDCl$_3$, δ ppm): −0.09, 135.37, 139.07.

IR Spectrum (KBr cm$^{-1}$): 2965, 1290, 1410, 1273, 1255, 1210, 1013, 782, 745.

Elementary Analysis: Calc'd: C, 37.35; H, 3.12. Found: C, 37.50; H, 3.18.

EXAMPLE 3

Preparation of poly[p-(chloromethylsilanylene)phenylene]

9.0 g (0.060 mole) of methyltrichlorosilane was added to p-phenylenedimagnesium chloride which had been prepared from 8.8 g (0.060 mole) of p-dichlorobenzene and 2.9 g (0.119 mole) of magnesium, in 120 ml of tetrahydrofuran (THF) in a nitrogen atmosphere, followed by heating to reflux for 35 hours.

Thereafter, the solvent was removed, the reaction solution was diluted with dry toluene/n-hexane, and insoluble salt was filtered off, to afford 9.0 g of an oily polymer of brown color. As a result of the following instrumental analysis, the polymer proved to be poly[p-(chloromethylsilanylene)phenylene] (unit 0.058 mole, 97%).

As to the molecular weight of the polymer, GPC measurement was performed after conversion of Si-Cl to Si-Me using methyllithium to find that Mw was 7,500 (degree of polymerization: about 55).

The following are the results of instrumental analysis of the poly[p-(chloromethylsilanylene)phenylene] obtained.

$^1$H-NMR Spectrum (in CDCl$_3$, 8 ppm): 0.42 (s, Si-CH$_3$), 7.02–7.80 (m, C$_6$H$_4$).

$^{13}$C-NMR Spectrum (in CDCl$_3$, 8 ppm): −0.85, 128.32, 128.91, 132.47, 132.88.

IR Spectrum (KBr cm$^{-1}$): 3060, 2958, 1440, 1270, 1253, 1205, 1155, 784, 752.

Elementary Analysis: Calc'd: C, 54.36; H, 4.56. Found: C, 52.51 H; 4.76.

EXAMPLE 4

Preparation of poly[p-(chlorophenylsilanylene)phenylene]

12.7 g (0.060 mole) of phenyltrichlorosilane was added to p-phenylenedimagnesium chloride which had been prepared from 8.8 g (0.060 mole) of p-dichlorobenzene and 2.9 g (0.119 mole) of magnesium in 120 ml of tetrahydrofuran (THF) in a nitrogen atmosphere, followed by heating to reflux for 35 hours.

Thereafter, the solvent was removed, the reaction solution was diluted with dry toluene/n-hexane, and insoluble salt was filtered off, to afford 12.2 g of an oily polymer of brown color. As a result of the following instrumental analysis, the polymer proved to be poly[p-(chlorophenylsilanylene)phenylene] (unit 0.056 mole, 94%).

As to the molecular weight of the polymer, GPC measurement was performed after conversion of Si-Cl to Si-Me using methyllithium to find that Mw was 11,000 (degree of polymerization: about 55).

The following are the results of instrumental analysis of the poly[p-(chlorophenylsilanylene)phenylene] obtained.

$^1$H-NMR Spectrum (in CDCl$_3$, 8 ppm): 6.78–7.70 (m, C$_6$H$_5$, C$_6$H$_4$).

$^{13}$C-NMR Spectrum (in CDCl$_3$, 8 ppm): 128.81, 128.93, 130.06, 131.65, 132.23, 136.01.

IR Spectrum (KBr cm$^{-1}$): 3053, 1235, 1205, 1251, 1207, 1120, 765, 742.

Elementary Analysis: Calc'd: C, 66.50; H, 4.19. Found: C, 66.72; H, 2.25.

EXAMPLE 5

Preparation of Poly[2,5-(chlorobenzylsilanylene)thienylene]

13.5 g (0.060 mole) of benzyltrichlorosilane was added to 2,5-thienylenedimagnesium chloride which had been prepared from 9.2 g (0.060 mole) of 2,5-dichlorothiophene and 2.9 g (0.119 mole) of magnesium in 120 ml of tetrahydrofuran (THF) in a nitrogen atmosphere, followed by heating to reflux for 20 hours.

Thereafter, the solvent was removed, the reaction solution was diluted with dry toluene, and insoluble salt was filtered off, to afford 9.2 g of an oily polymer of yellowish brown. The polymer was then subjected to the same analyses as in Example 1, including $^1$H-NMR, $^{13}$C-NMR, IR and elementary analysis, to find that the polymer was poly[2,5-(chlorobenzylsilanylene)thienylene] (unit 0.020 mole, 66%).

As to the molecular weight of the polymer, GPC measurement was performed after conversion of Si-Cl to Si-Me using methyllithium to find that Mw was 3,500 (degree of polymerization: about 15).

EXAMPLE 6

Preparation of [2,5-(chlorophenylsilanylene)thienylene]

A solution (1.6M, 75 ml, 0.120 mole) of n-butyllithium in hexane was dropwise added slowly into a solution of 12.0 g (0.120 mole) N,N,N′,N′-tetramethylethylenediamine (TMEDA) and 5.1 g (0.060 mole) thiophene in 120 ml n-hexane, in a nitrogen atmosphere, followed by heating to reflux for 2 hours, to prepare 2,5-thienylenedilithium, into which was then added 9.2 g (0.060 mole) of phenyltrichlorosilane), followed by heating to reflux for 5 hours.

Thereafter, the solvent was removed, the reaction solution was diluted with dry toluence/n-hexane, and insoluble salt was filtered off, to afford 11.1 g of an oily polymer of yellowish brown. As a result of the following instrumental analysis, the polymer proved to be poly[2,5-(chlorophenylsilanylene)thienylene] (unit 0.050 mole, 83%).

As to the molecular weight of the polymer, GPC measurement was made after conversion of Si-Cl to Si-Me using methyllithium to find that Mw was 6,100 (degree of polymerization: about 30).

The following are the results of instrumental analysis of the poly[2,5-(chlorophenylsilanylene)thienylene] obtained.

$^1$H-NMR Spectrum (in CDCl$_3$, 8 ppm): 6.65–7.81 (m, C$_4$H$_2$S, C$_6$H$_5$).

$^{13}$C-NMR Spectrum (in CDCl$_3$, 8 ppm): 127.83, 128.19, 134.20, 132.63, 138.71, 139.39.

IR Spectrum (KBr cm$^-$): 3080, 2951, 2882, 1291, 1235, 1275, 1252, 1211, 1020, 818, 746, 702.

Elementary Analysis: Calc'd: C, 53.92; H, 3.17. Found: C, 54.03; H, 2.97.

EXAMPLE 7

Preparation of poly[2,5-(chloro-t-butylsilanylene)thienylene]

A solution (1.6M, 75 ml, 0.120 mole) of n-butyllithium in hexane was dropwise added slowly into a solution of 14.0 g (0.120 mole) N,N,N′,N′-tetramethylethylenediamine (TMEDA) and 5.1 g (0.060 mole) thiophene in 120 ml n-hexane, in a nitrogen atmosphere, followed by heating to reflux for 4 hours, to prepare 2,5-thienylenedilithium, into which was then added 11.5 g (0.060 mole) of t-butyltrichlorosilane, followed by heating to reflux for 5 hours.

Thereafter, the solvent was removed, the reaction solution was diluted with dry toluene, and insoluble salt was filtered off, to yield 9.8 g of an oily polymer of yellowish brown. The polymer was then subjected to the same analyses as in Example 1, including $^1$H-NMR, $^{13}$C-NMR, IR and elementary analysis, to find that the polymer was poly[2,5-(chloro-t-butylsilanylene)thienylene].

As to the molecular weight of the polymer, GPC measurement was made after conversion of Si-Cl to Si-Me using methyllithium to find that Mw was 2,400 (degree of polymerization: about 13).

What is claimed is:

1. A silicon-containing organic compound represented by the following general formula [1]:

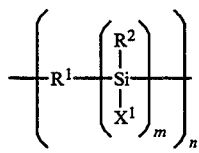
(1)

where $R^1$ is a π conjugated type divalent organic group having 2 to 30 carbon atoms, $R^2$ is a hydrocarbon group having 1 to 30 carbon atoms, $X^1$ is a halogen atom, m and n satisfy the conditions of $1 \leq m \leq 2$ and $n \geq 2$, respectively.

2. A compound as set forth in claim 1, wherein $R^1$ is a substituted or unsubstituted hydrocarbon residue having 2 to 30 carbon atoms and selected from allylene, heteroallylene, vinylene, butadienylene, ethynylene and butadiynylene groups, or a combination thereof.

3. A compound as set forth in claim 2, wherein the allylene group is p-phenylene, m-phenylene, 2,4-naphthylene, 2,5-naphthylene, 2,6-naphthylene, 4,4'-biphenylene, 9,10-anthrylene, or 2,7-pyrenylene.

4. A compound as set forth in claim 2, wherein the heteroallylene group is 2,5-thienylene, 2,5-furanylene, 2,5-pyrolylene, or 1,3-benzo[c]thienylene.

5. A compound as set forth in claim 1, wherein $R^1$ is alkyl, aryl, or aralkyl.

6. A process for preparing a silicon-containing organic compound represented by the following general formula [1]:

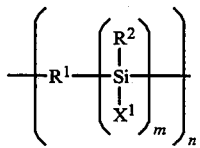
(1)

where $R^1$ is a π conjugated type divalent organic group having 2 to 30 carbon atoms, $R^2$ is a hydrocarbon group having 1 to 30 carbon atoms, $X^1$ is a halogen atom, m and n satisfy the conditions of $1 \leq m \leq 2$ and $n \geq 2$, respectively, which process is characterized by reacting an organometallic compound represented by the following general formula [2]:

$$M^1\text{-}R^1\text{-}M^2 \quad [2]$$

where $R^1$ is a π conjugated type divalent organic group having 2 to 30 carbon atoms, $M^1$ and $M^2$, which may be the same or different, are each a metal group selected from Group 1, 2 and 12 metals in the Periodic Table, with a silane compound represented by the following general formula [3]:

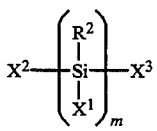
[3]

where $R^2$ is a hydrocarbon group having 1 to 30 carbon atomps, $X^1$, $X^2$ and $X^3$ are each a halogen atom and m satisfies the condition of $1 \leq m \leq 2$.

* * * * *